US007892594B2

(12) United States Patent
Luk et al.

(10) Patent No.: US 7,892,594 B2
(45) Date of Patent: Feb. 22, 2011

(54) ENHANCED BIO-ASSAYS BY USING GRADIENT NANOTOPGRAPHY

(75) Inventors: Yan Yeung Luk, Manlius, NY (US);
Karen A. Simon, Syracuse, NY (US);
Erik A. Burton, Phoenix, NY (US);
Prerli Sejwal, Syracuse, NY (US);
YongBin Han, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 1085 days.

(21) Appl. No.: 11/562,022

(22) Filed: Nov. 21, 2006

(65) Prior Publication Data
US 2008/0199950 A1 Aug. 21, 2008

Related U.S. Application Data

(60) Provisional application No. 60/739,904, filed on Nov. 23, 2005.

(51) Int. Cl.
*G01N 1/28* (2006.01)
(52) U.S. Cl. .................. 427/2.11; 349/123; 427/2.12; 427/2.13
(58) Field of Classification Search .................. 349/123; 427/2.11
See application file for complete search history.

(56) References Cited

U.S. PATENT DOCUMENTS
2003/0071949 A1 * 4/2003 Abbott et al. ............... 349/123

* cited by examiner

*Primary Examiner*—Michael Barr
*Assistant Examiner*—Andrew Bowman
(74) *Attorney, Agent, or Firm*—George R. McGuire; David L. Nocilly; Bond Schoeneck & King, PLLC

(57) ABSTRACT

A system and method for using gradient nanotopography to increase mammalian cell attachment and cell confinement on surfaces. A surface platform consisting of a thin film of gold possessing a gradient of topography on the surface and self-assembled monolayers of alkanethiols presenting desired functional groups is formed. A gradient in the chemical properties is induced in the terminal groups of the monolayer because of the continuous increase in the surface area and the anisotropy of gold film structure. The gradient nanotopraphy provides simultaneous control of two key properties, the presentation of the terminal functional groups and a continuous increase in the surface density of functional groups on the surface. This control provides for drug screening assays using adherent cell-based experiments.

10 Claims, 16 Drawing Sheets

ENHANCED BIO-ASSAYS BY USING GRADIENT NANOTOPGRAPHY

CROSS-REFERENCE TO RELATED APPLICATIONS

The present application claims priority to U.S. Provisional Application No. 60/739,904, filed on Nov. 23, 2005.

BACKGROUND OF THE INVENTION

1. Field of Invention

The present invention relates to gradient nanotopography and, more specifically, to a system and method for continuously increasing mammalian cell attachment and cell confinement on a single surfaces.

2. Description of Prior Art

Recent attempts to replicate the natural development of mammalian cells in a laboratory involve experimenting with the effects of changes in the topography of the surrounding environment. For example, nanotopographic changes in the in the surfaces of a cell's surroundings can profoundly change the way that the cells propagate. The study of the effects of natural nanotopographic surfaces typically involves the creation of artificial structures using compounds that are easily adapted for forming different nanotopographic structures. These compounds are not, however, necessarily well adapted for accepting and propagating cellular materials. Accordingly, there is a need for the creation of improved structures for the study and development of mammalian cells on surfaces of varying nanotopographic design.

3. Objects and Advantages

It is a principal object and advantage of the present invention to provide a system and method for improving cell attachment to surfaces.

It is an additional object and advantage of the present invention to provide a system and method for improving cell confinement to surfaces.

It is a further object and advantage of the present invention to provide a system and method for screening functional peptides for axonal guidance for nerve regeneration.

It is also an object and advantage of the present invention to provide a system and method for fabricating a biodegradable gel possessing a protein gradient to assist regenerating injured nerves.

It is also an object and advantage of the present invention to provide a system and method for presenting a gradient in the chemical properties of the surface materials on a single surface.

Other objects and advantages of the present invention will in part be obvious, and in part appear hereinafter.

SUMMARY OF THE INVENTION

The present invention comprises a system and method for using gradient nanotopography to increase mammalian cell attachment and cell confinement on surfaces. The system includes a surface platform consisting of a thin film of gold possessing a gradient of topography on the surface and self-assembled monolayers (SAMs) of alkanethiols presenting desired functional groups. Because of the continuous increase in the surface area, a chemical gradient is induced in the terminal groups of the monolayer. This chemical gradient is unique from all other previously known chemical gradient because of the simultaneous control of two key properties. First, the presentation of the terminal functional groups is uniform due to the close packing and well-ordered nature of the self-assembled monolayer. Second, there is a continuous increase in the surface density of functional groups on the surface due to the underlying gradient topography at nanometer-scale.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
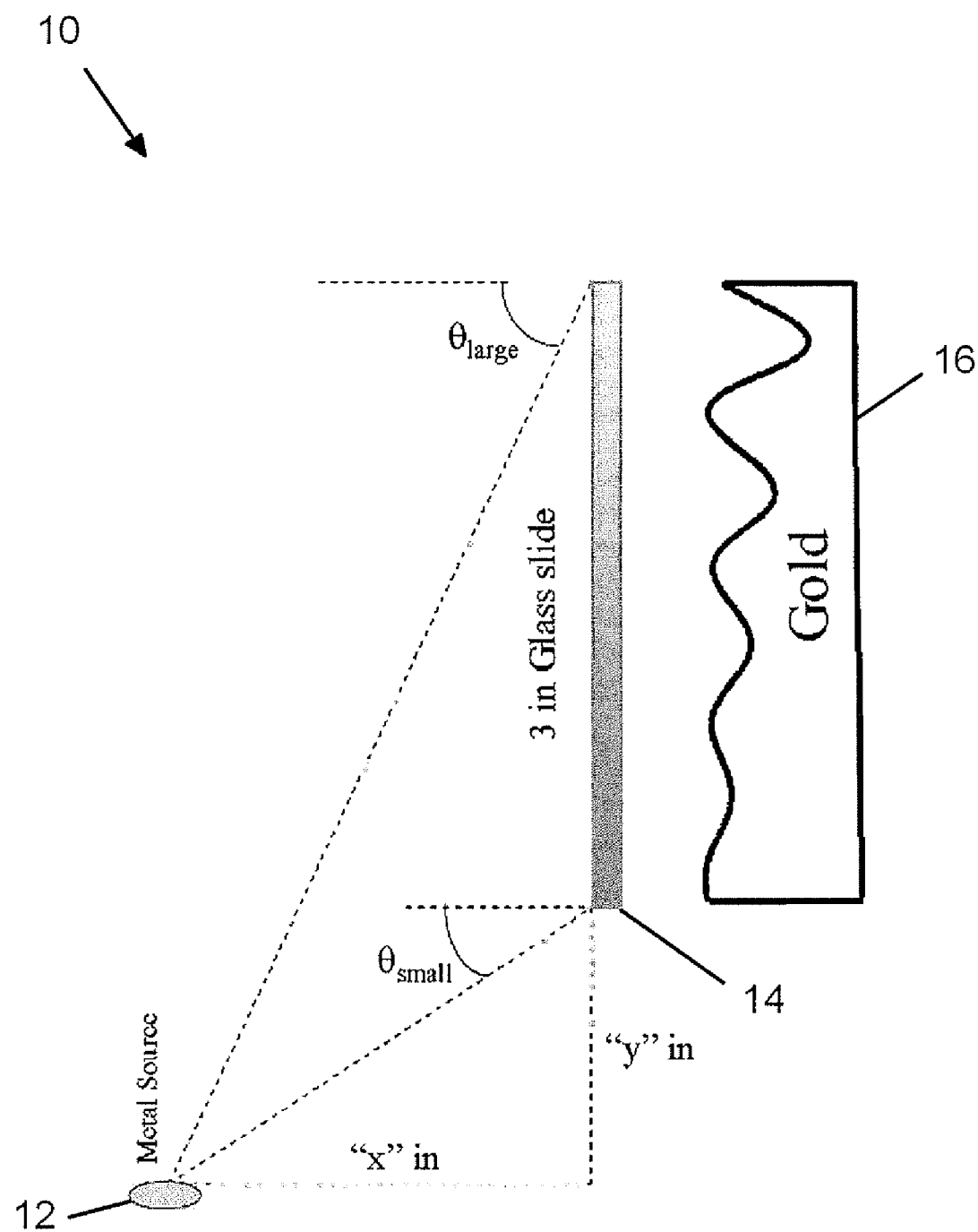
FIG. 1 is a schematic of gradient nanotopography according to the present invention.
Figure 2:
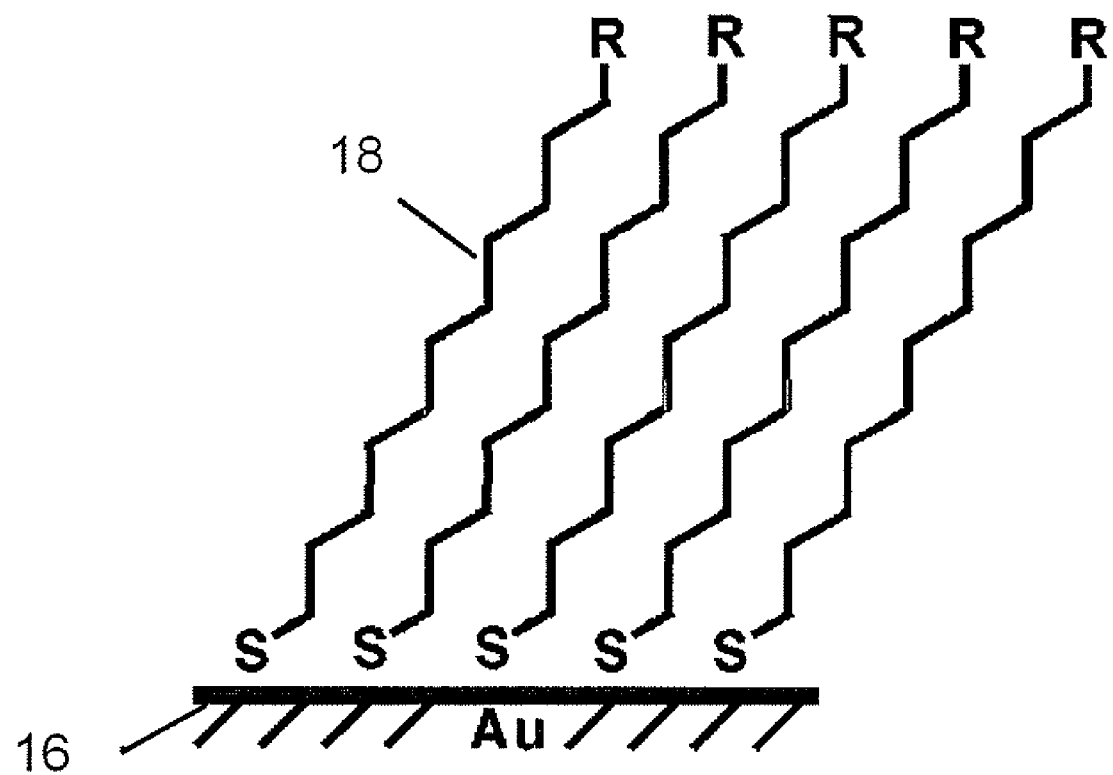
FIG. 2 is a schematic of self-assembled monolayers of alkanethiols on gold films according to the present invention.

Referring now to the drawings, wherein like numerals refer to like parts throughout, there is seen in FIG. 1 a system 10 according to the present invention for generating gradient nanotopography. System includes a metal source 12 for depositing a thin film of metal, such as gold, onto a glass slide 14. Source 12 is aligned to apply the metal onto slide 14 at a continuously increasing angle of incidence measured from the normal of the slide, thereby a gold film 16 having a varying nanotopographic design according to the present invention. As seen in FIG. 2, the geometry of the present invention may be used to support a self-assembled monolayer (SAM) 18 of alkanethiols on the gold film 16 of slide 14.

Figure 3:
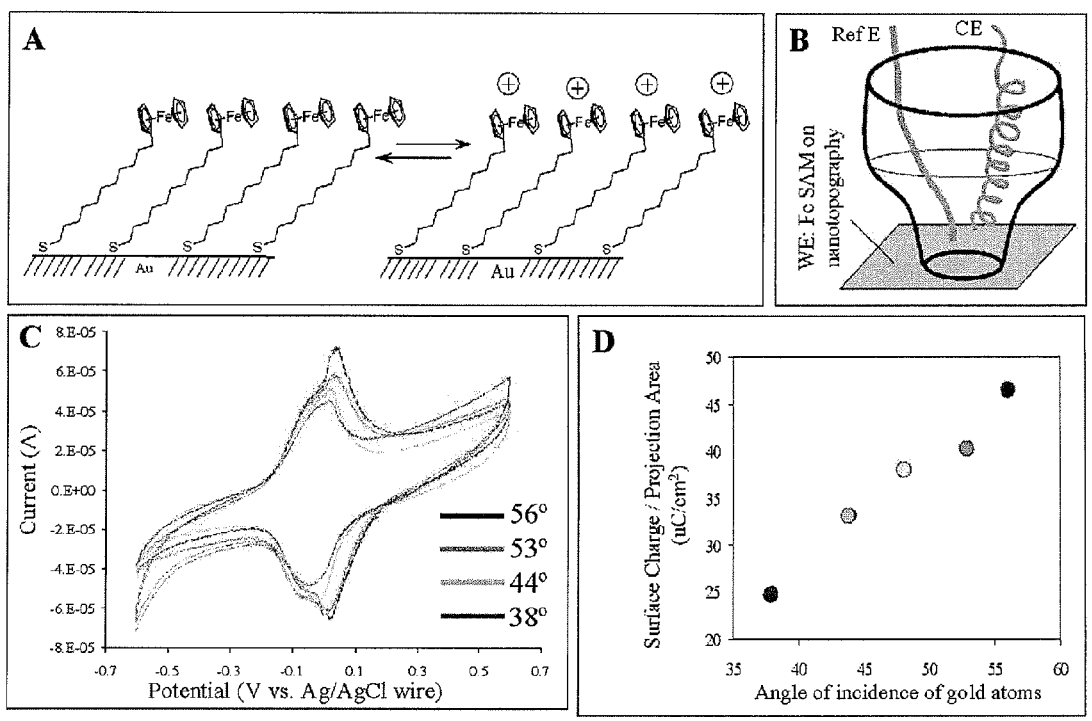
FIGS. 3A-3D are schematics of one electron redox coupling of ferrocene terminated SAMs on gold films according to the present invention.

Referring to FIG. 3, the present invention also comprises a one-electron redox (oxidation and reduction) of a ferrocene-terminated monolayer on the gradient nanotopography. By measuring the redox activity of a ferrocene-terminated monolayer (see FIG. 3A), the surface density of alkanethiols on gradient gold films deposited at an oblique angle varying from 37 to 59 degrees over a distance of 7 cm are quantitatively measured. Because the ferrocene undergoes a reversible one-electron redox process, the charge measured under the oxidative (or reductive) wave of a cyclic voltammogram is directly proportional to the number of ferrocene-terminated alkanethiols on the actual surface area on the gold film (surface charge×$6.24×10^{18}$=# of molecules). In order to measure the charges of ferrocene redox along the steepness of the gradient nanotopography, a fixed projection area of 0.95 cm$^2$ of the SAM is exposed to the electrolyte for cyclic voltammetry (see FIG. 3B).

FIG. 3C shows five cyclic voltamograms of the redox of ferrocene SAM on five different positions on a single gradient gold filmc corresponding to the angle of depositions at 38°, 44°, 48°, 53° and 56° measured from the normal of the slide. Integration of the charge under the oxidative current of the ferrocene SAM indicates that the surface charge per projection area increases as the angle of the gold deposition increases (FIG. 3D). This result indicates that there is a continuous increase in the surface load of self-assembled monolayer from $1.56×10^{14}$ alkanethiols on gold films deposited at 38° to $2.92×10^{14}$ alkanethiols on gold films deposited at 56° (see Table 1 below). This corresponds to 88% increase in the surface load of alkanethiols over a 7 cm glass slide. This result is also consistent with uniformly deposited gold films at 0° from the normal of the slide, where the surface charge per projection area is the smallest, and also indicates that large angle of gold incidence causes a high degree of topography and large surface area.

Figure 5:
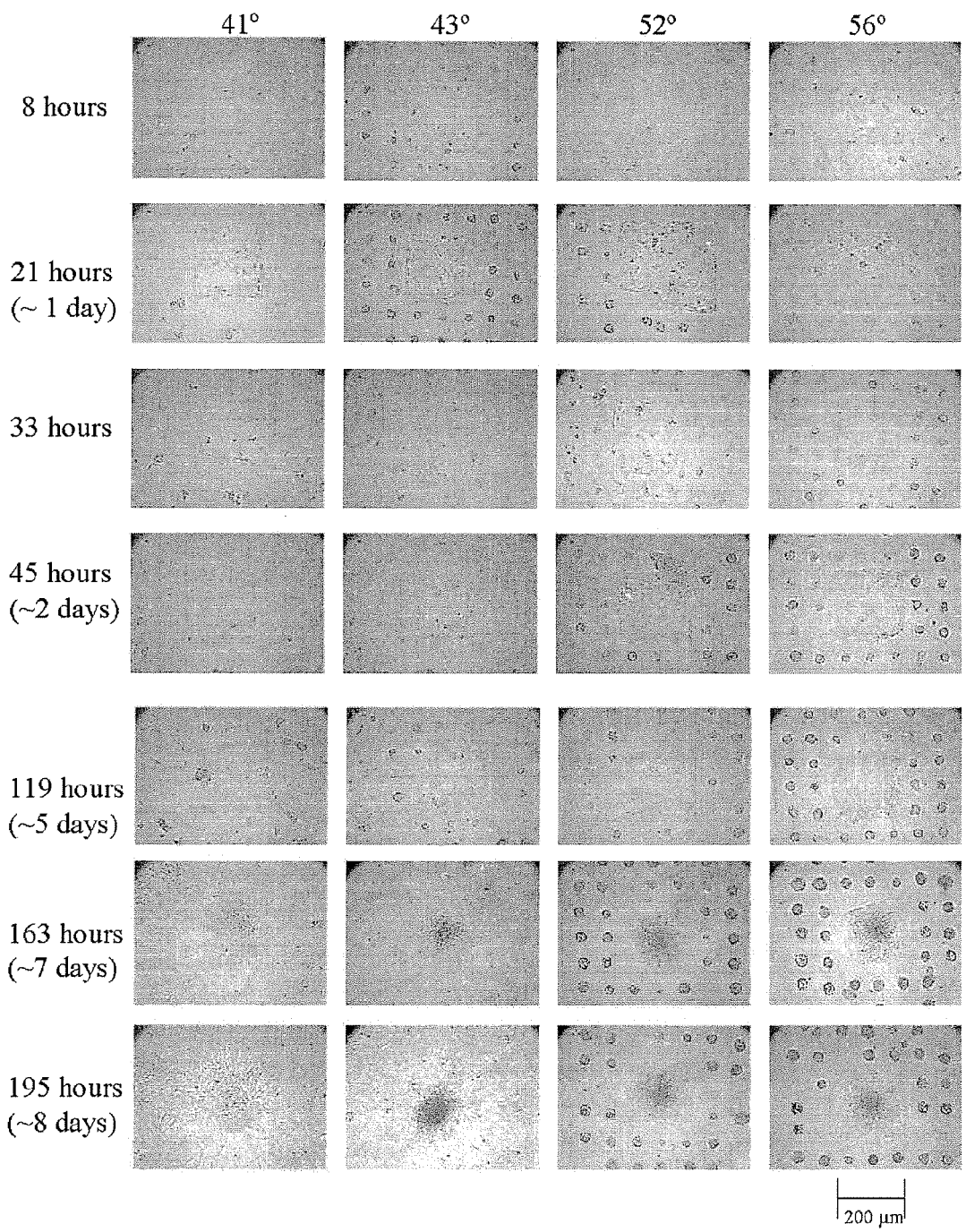
FIG. 5 is an optical micrograph of fibroblast cells according to the present invention.

Referring to FIG. 5, mammalian 3T3 fibroblast cells attach and reach confluency within squares 20 more rapidly on the region of large angle of gold deposition (high topography) than on the region of small angle of gold deposition (low topography). After cells grow confluent on all squares 20 on the gradient nanotopography, cells are confined longer on high topography than on low topography regions. As a result, gradient nantopograpy according to the present invention provides a significant advantage for using carefully crafted nanotopography to do cell biology and cell-based biotechnology.

The longer confinement of cells on high topography is particularly useful because the cells reach confluency sooner on high topography than low topography, and thus have a larger over population pressure to proliferate into the surrounding bio-inert areas. Even though the local packing of tri(ethylene glycol) alkanethiols are the same on the polycrystalline facets on for both high and low density topography, the surface density of tri(ethylene glycol) alkanethiols is larger on high topography than low topography when compared at a large scale (perhaps hundreds of nanometers and beyond). Cells continuously secrete fibronectin into the close proximate space in the culture medium, which over long period of time can foul the bio-inertness of the tri(ethylene glycol) SAMs in the close proximity. On the high topography, there is a larger surface density of tri(ethylene glycol) alkanethiols than on the low topography. Therefore, confined cells take longer to overcome the surrounding bio-inertness than low topography.

Figure 6:
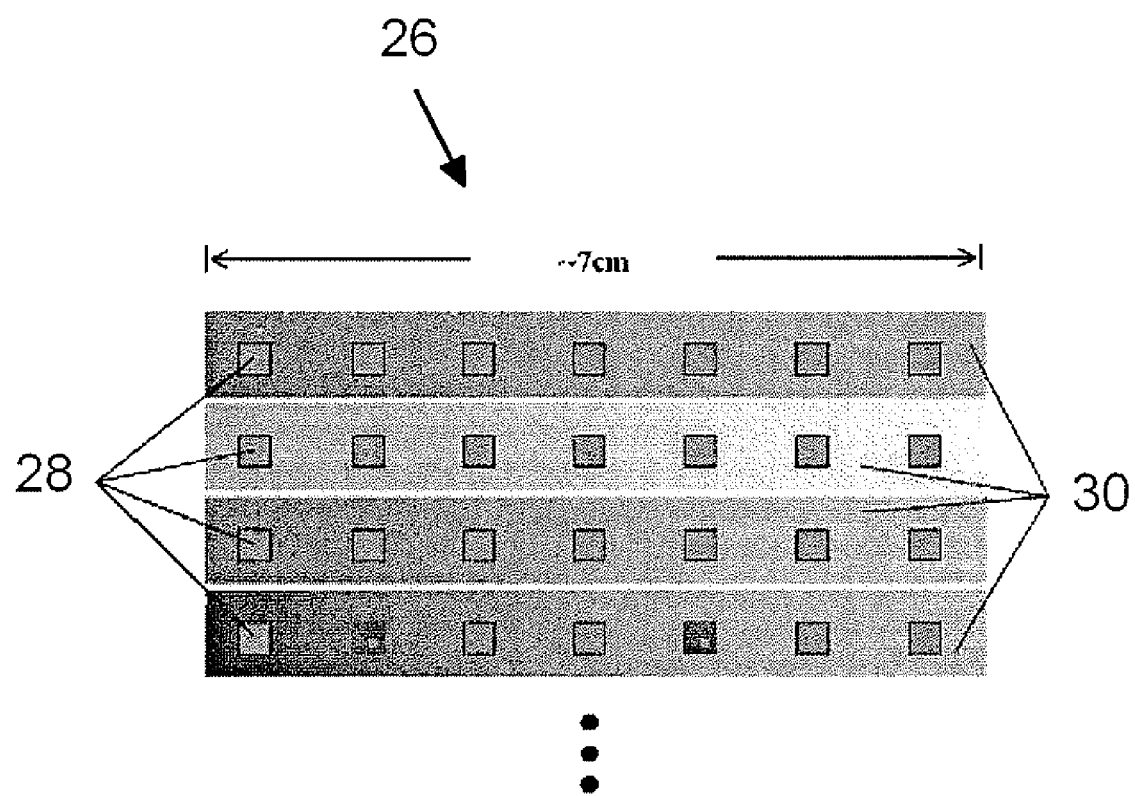
FIG. 6 is a schematic of a drug screening assay for identifying drugs that can induce axon growth of neuron cell according to the present invention.
Figure 7:
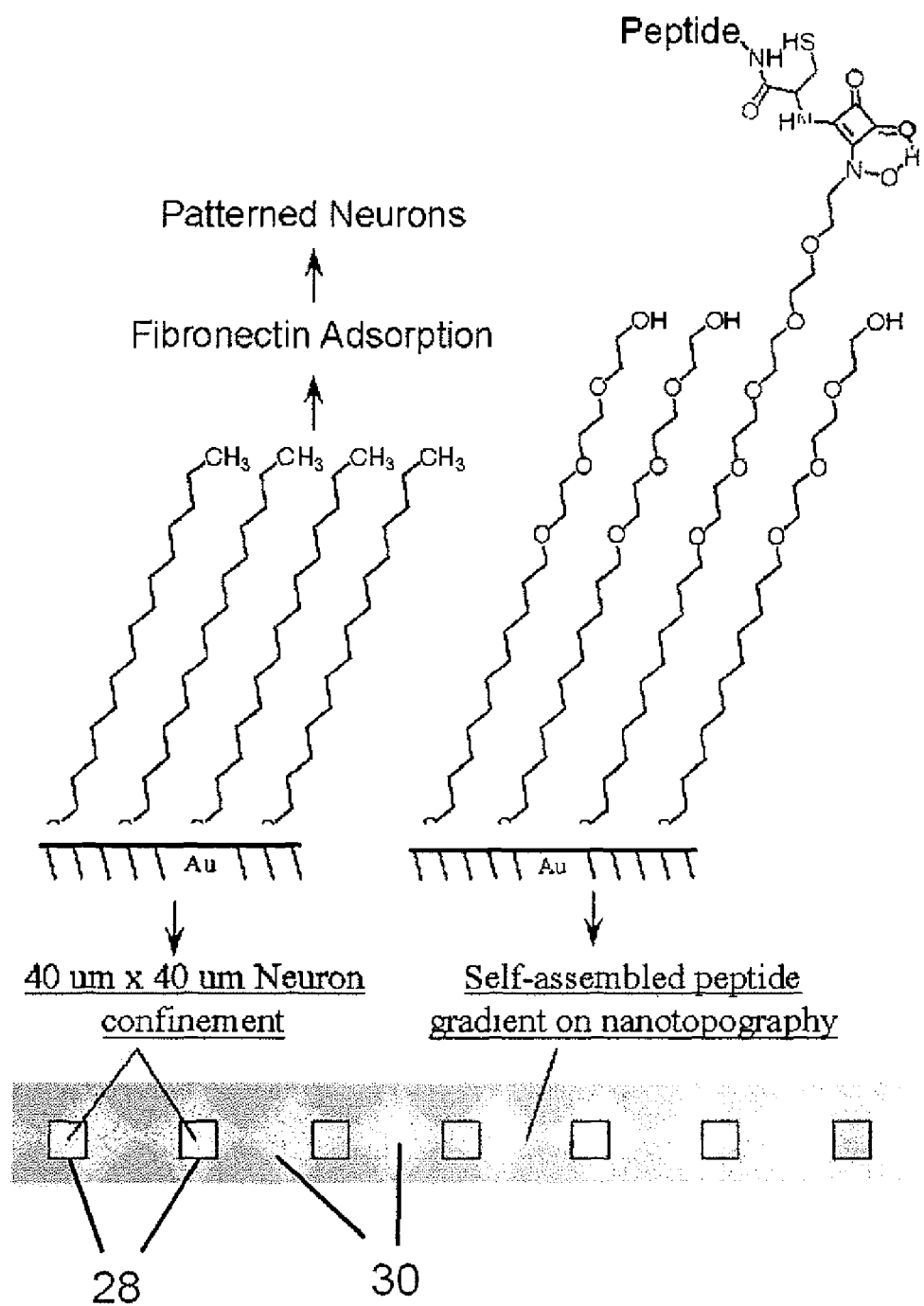
FIG. 7 is a schematic of axonal guidance experiment on gradient nanotopography according to the present invention.

Referring to FIG. 6, the present invention may be applied to a screening assay 26 for peptides or other drugs to guide the growth cone extension for nerve regeneration. A linear array of neuron cells are cultured using confined squares 28 amidst a self-assembled gradient of candidate peptides 30 that have the potential to guide the extension of the growth cone of the axon of the neuron cell. The details of the surface design of assay 26 is seen in FIG. 7. Because the oligo(ethylene glycol) background in the gradient peptide region will resist cell

TABLE 1

The surface charge and the number of ferrocene alkanethiols per projection area on the gradient nanotopography.

| Angle of Deposition (degree) | $^a$56 | $^a$53 | $^a$48 | $^a$44 | $^b$40 | $^a$38 | $^c$0 |
|---|---|---|---|---|---|---|---|
| Surface charge/project area (uC/cm$^2$) | 46.7 | 40.1 | 38.1 | 33.2 | 29.4 | 24.9 | 21.4 |
| # alkanethiols/project area (×10$^{14}$/cm$^2$) | 2.92 | 2.56 | 2.38 | 2.07 | 1.83 | 1.56 | 1.34 |

$^a$gradient deposition of gold on a single glass slide
$^b$oblique deposition
$^c$uniform deposition of gold films: the gold atoms incident at normal of the glass slide while the glass was rotating during the deposition process.

Figure 4:
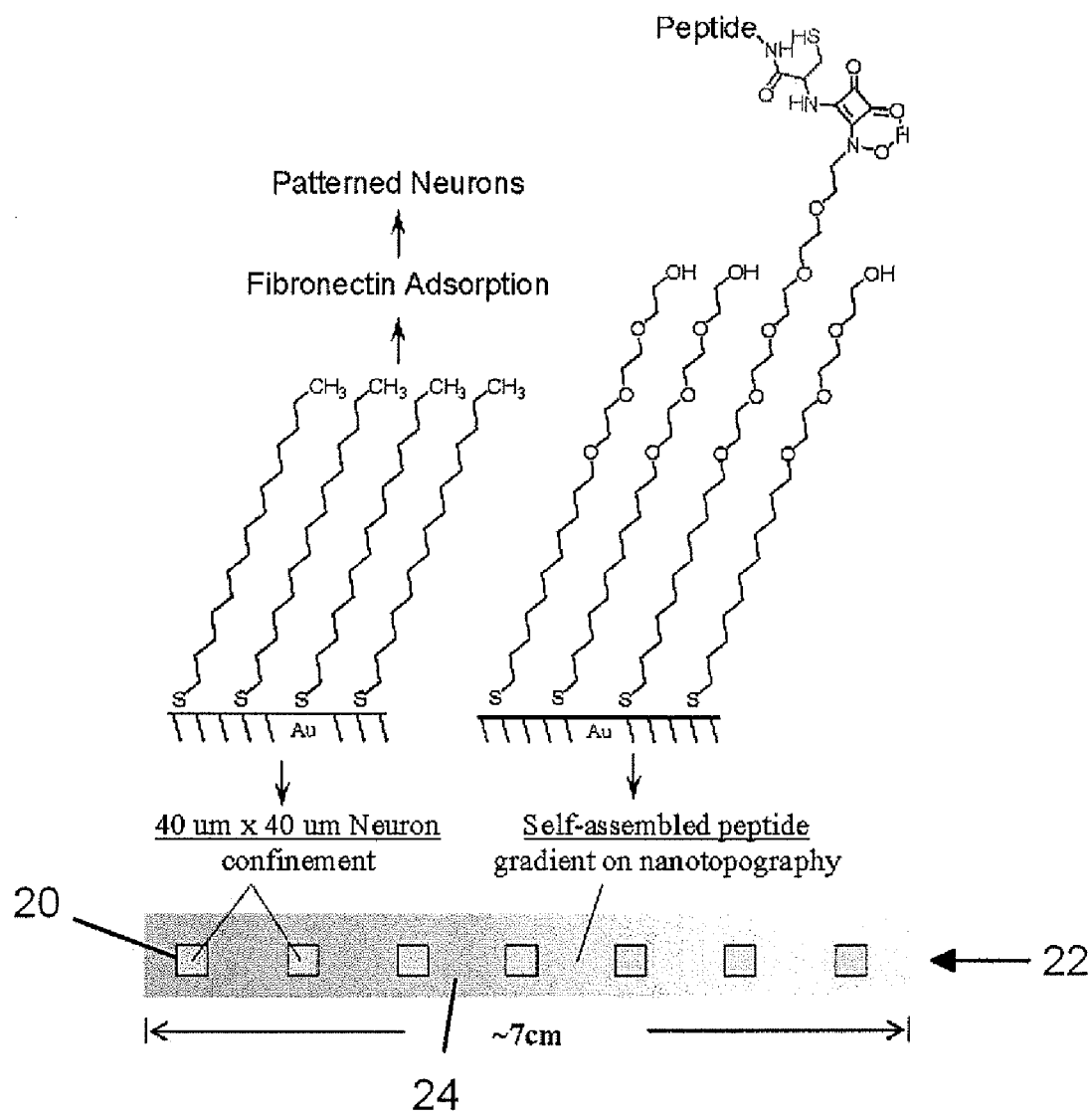
FIG. 4 is a schematic of a patterned substrate which controls cell adhesion and confinement according to the present invention.

Referring to FIG. 4, the present invention provides enhanced cell adhesion and confinement on the gradient nanotopography. By using microcontact printing, it is possible to create patches of cell adhesion areas (HS(CH$_2$)$_{14}$CH$_3$) in μm-size squares 20 along the gradient steepness 22, and surround these patches with a bio-inert chemistry (HS(CH$_2$)$_{12}$(OCH$_2$CH$_2$)$_3$OH) background 24 that resists protein adsorption and cell adhesion. The methyl-terminated SAM squares 20 support protein adsorption, and thus promote cell attachment and adhesion. The bio-inert background 24 of triethyleneglycol-terminated SAMs resists protein adsorption, and theefore confines cells within the methyl-terminated SAM squares 20.

adhesion and migration, any observed axon growth outside the squares of cell adhesive region is a unique response to the gradient of the candidate peptides decorated on the surface.

The present invention may also be used for reversible driving of aqueous droplet movement on surfaces used for microfluidics applications. Controlling solution movement and mixing is a key requirement for studying and utilizing microfludics in various applications. Because the surface-to-volume ratio becomes very large at micrometer-scale, the effect of surface can overwhelmingly dominate the flow properties such as laminar versus turbulent mode of flow. Gradient nanotopography according to the present invention provides a unique opportunity to control both the surface chemistry and the driving force used to control the flow. Using redox active SAMs, the gradient in surface density of alkanethiols on the nanotopography will generate reversibly a gradient of surface charges by electrochemical control in real time.

Figure 8:
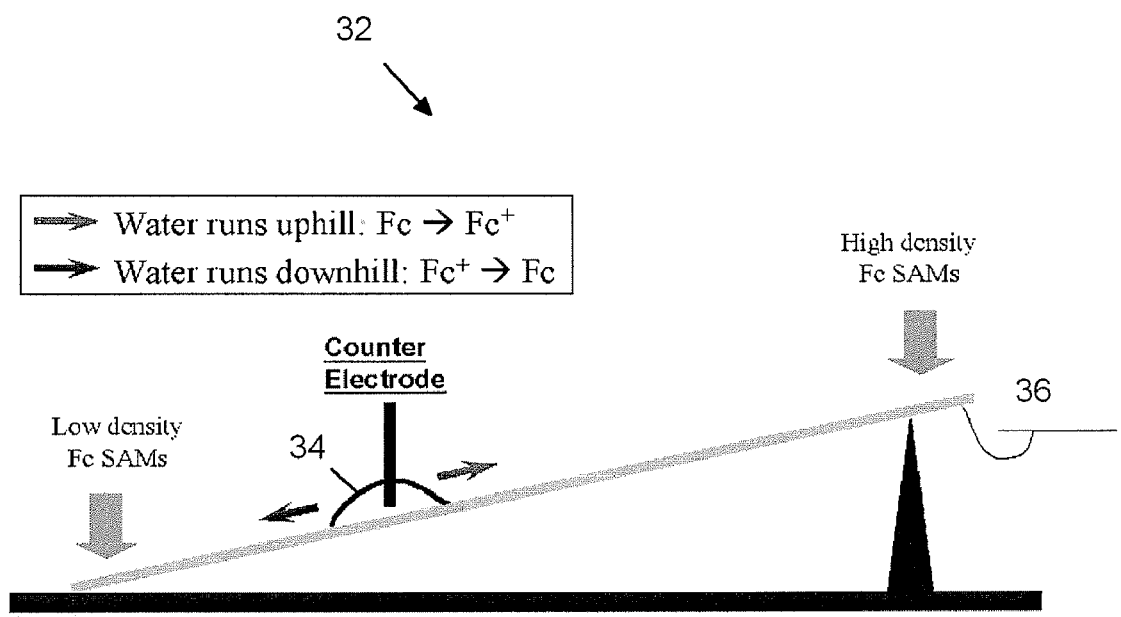
FIG. 8 is a schematic of the experimental setup for driving water uphill and downhill reversibly by electrochemical control of gradient surface charges according to the present invention.

There is seen in FIG. 8 a device 32 using gradient nanotopography and surface charges to drive a grounded water droplet 34 uphill along by oxidizing a gradient of ferrocene (Fc) SAMs formed according to the present invention on a working electrode 36 to form ferrocenium (Fc$^+$) SAMs. If the higher density of ferrocene is poisoned at the uphill side, oxidation of Fc to Fc$^+$ will create a higher surface charge there that will pull the water droplet upward. As ferrocenium is reduced back to ferrocene, the water droplet will run downhill by both gravity and the increased hydrophobicity at the uphill side. This control of water mobility on surface provides a mechanism for the control of a water droplet in microfluidic apparatuses.

Figure 9:
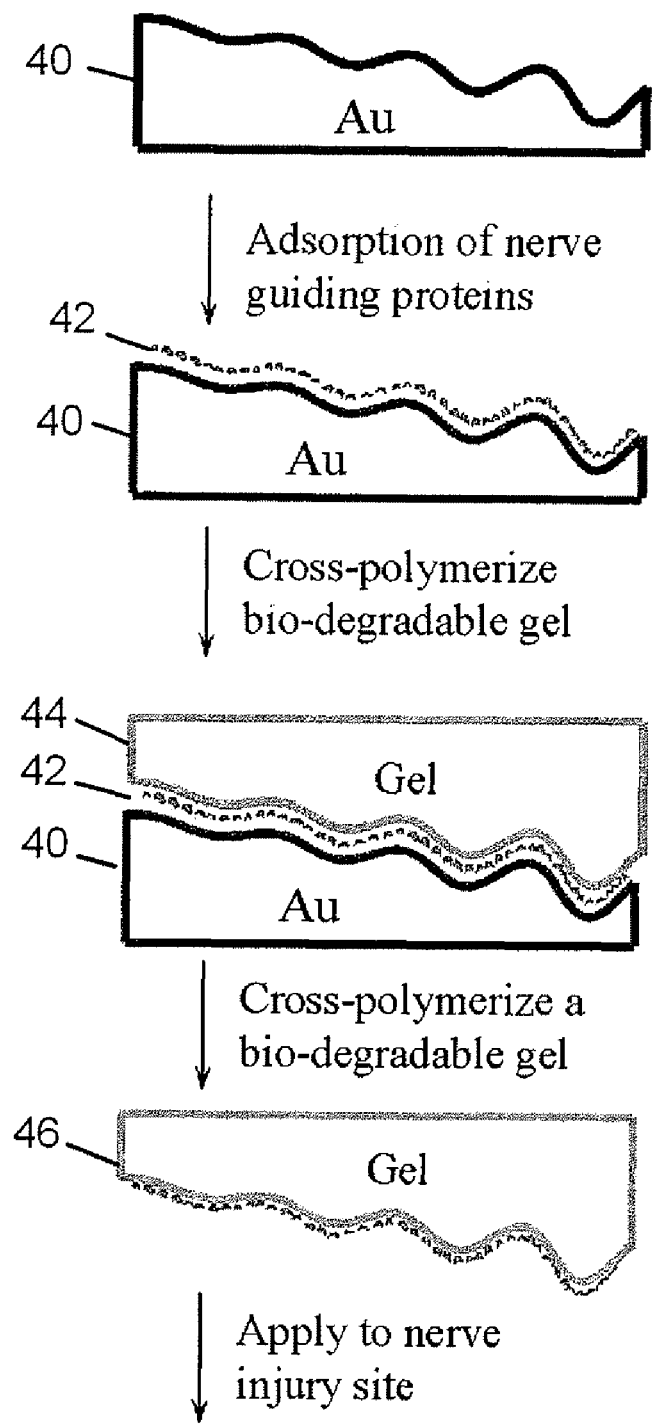
FIG. 9 is a schematic of the fabrication of a biodegradable gel for use as implantable guidance to regenerate injured nerves according to the present invention.

Referring to FIG. 9, the present invention may be used to fabricate a biodegradable gel possessing a protein gradient. The gel may be used as implantable device to assist regenerating injured nerves. First, a surface/substrate with gradient nanotopography 40 according to the present invention is used as a mold to immobilize a gradient of chemotropic guidance proteins 42 that promote nerve regeneration at an injured site. When a substrate with gradient nanotopography according to the present invention is submerged into a solution of nerve regenerating guidance proteins, the high topography supports more protein adsorption and the low topography supports less protein adsorption. Because the gradient nanotopography continuously increases in surface area, the concentration of the absorbed protein molecules increases as the topography of the surface increases. Once a gradient of protein molecules are adsorbed unto the surface, a biodegradable polymer 44 is cross-linked to form a gel 46 positioned on protein gradient 42. Protein gradient 42 will then be partly imbedded into gel 44. Gel 44 is then peeled off from the gradient nanotopography surface 40, including the partly imbedded protein gradient 42.

Gel 44 thus contains a gradient of chemotropic guidance proteins 42 that may be used as a bio-degradable "bandage" for the regeneration of nerve cells by promoting axon migration on the site of injury. This bio-degradable "bandage" is implanted to serve as a "bridge" on the region of the lesion to facilitate and hasten the process of nerve regeneration and thus the recovery of the injury. The use of biodegradeable gel 46 is also convenient and practical since a follow-up surgery preceding the treatment is not needed. Once it has served its function, gel 46 can be slowly degraded in the body. The fabrication of a bio-degradable "bandage" according to the present invention is helpful in the treatment of spinal cord injuries (SPI) or central nervous system-related damages wherein recovery is too slow or almost unattainable due to the inefficiency or failure of the central nervous system to regenerate nerve cells. With the development of such an implant, the possibility of prolonged or permanent paralysis of SPI victims can be prevented or minimized.

Figure 10:
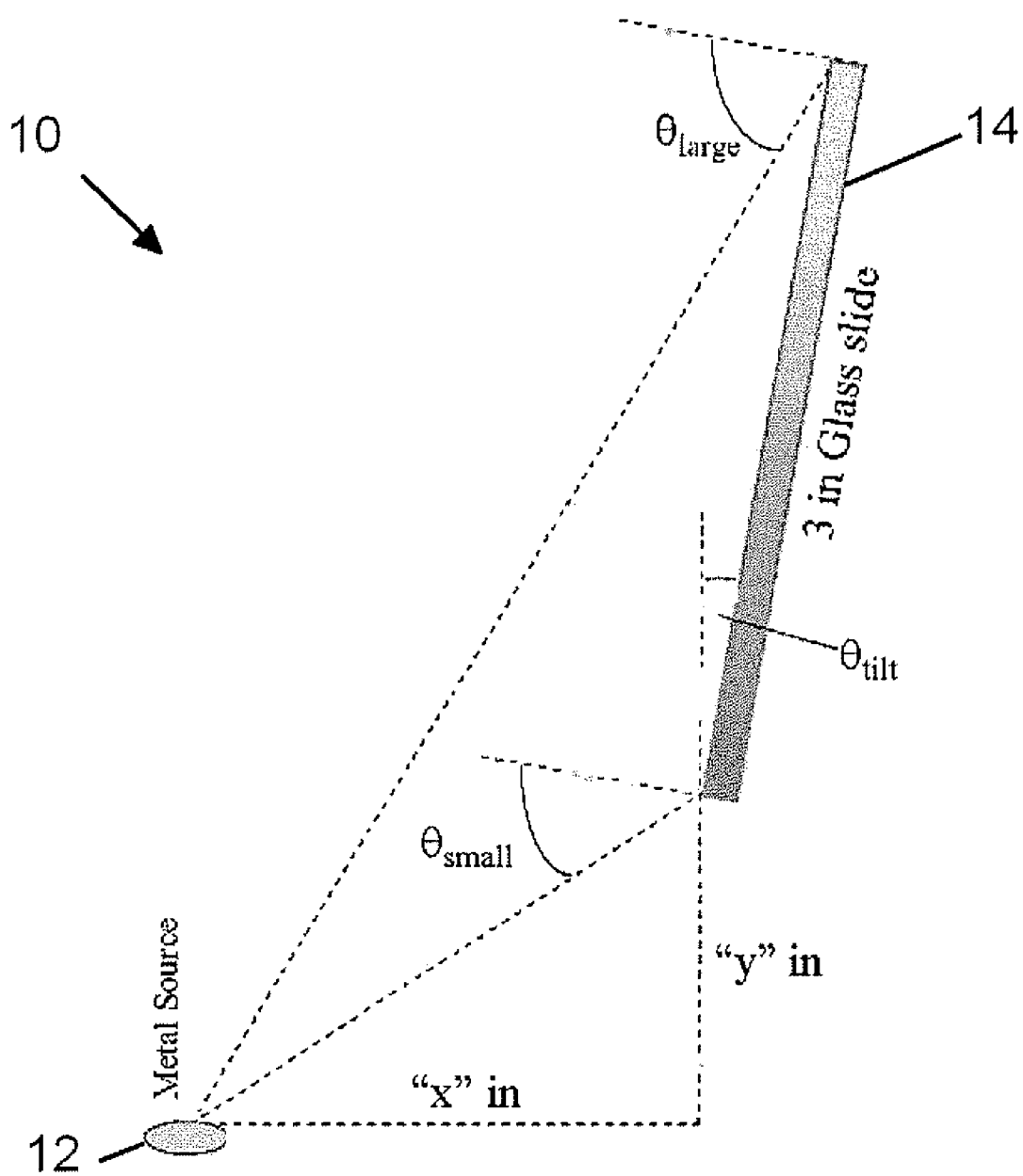
FIG. 10 is a schematic of a tilted geometry of the gold deposition that affords a steeper gradient profile according to the present invention.

Referring to FIG. 10, system 10 according to the present invention for generating gradient nanotopography may be adjusted to increase the steepness of the gradient nanotopography by applying a tilted geometry of vapor deposition of the thin film metal 16 to slide 14. Compared to a strictly vertical setup, as seen in FIG. 1, tilting the glass slide slightly allows for a steeper gradient.

Figure 11:
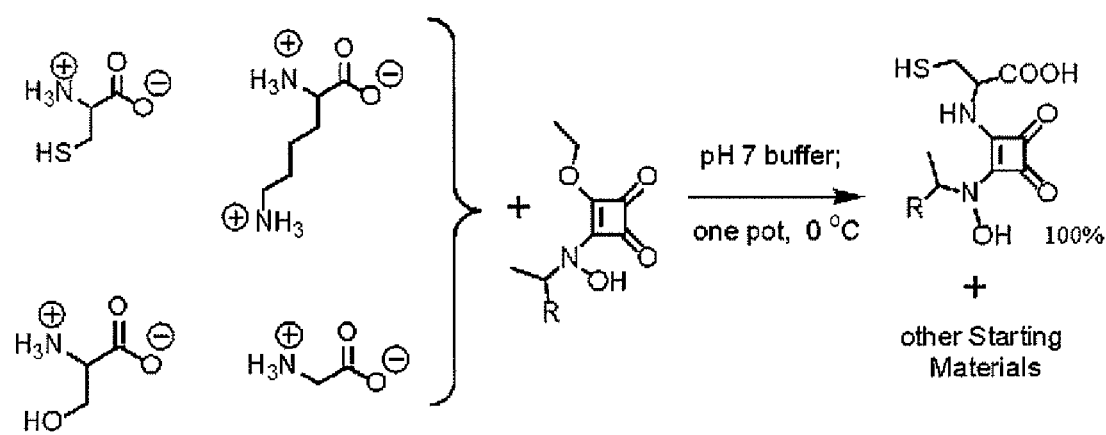
FIG. 11 is a schematic of a method of using chemoselective chemistry to immobilize peptides or proteins according to the present invention.
Figure 12:
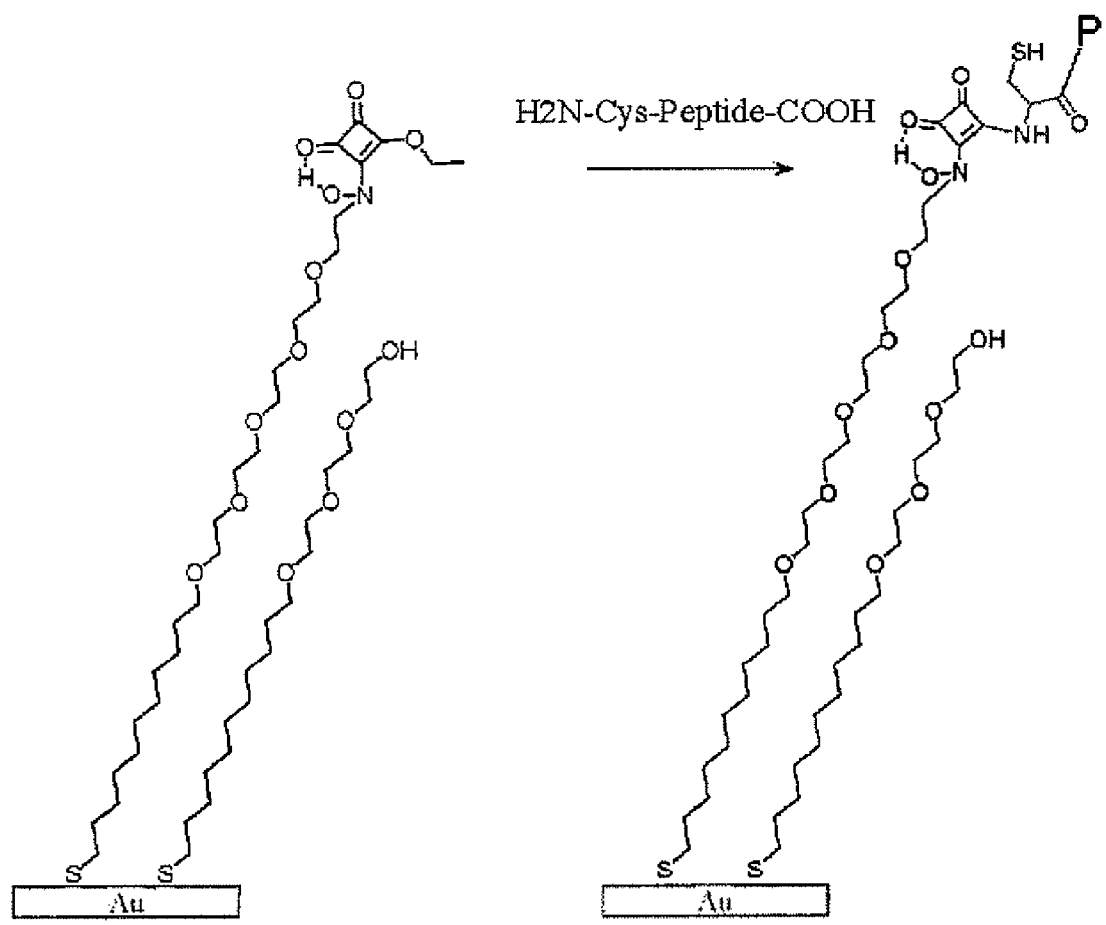
FIG. 12 is a schematic of immobilizing peptides on bioinert SAMs for making a peptide gradient for cell adhesion studies according to the present invention.
Figure 12A:
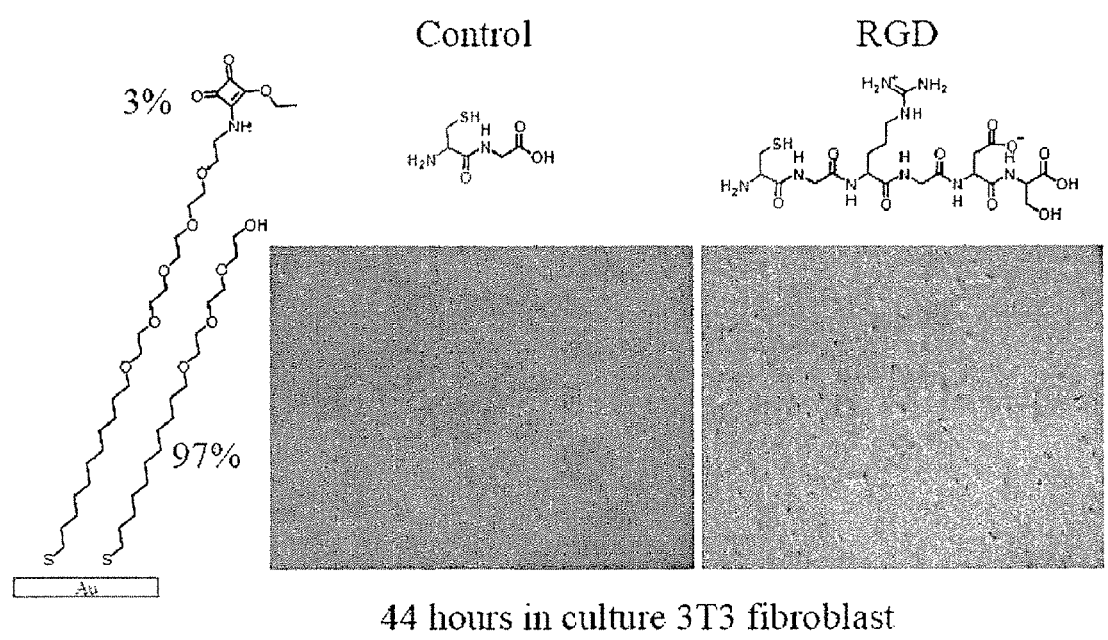
FIG. 12A is demonstration of the immobilization of mammalian cells 3T3 fibroblast using chemoselective chemistry according to the present invention.
Figure 13:
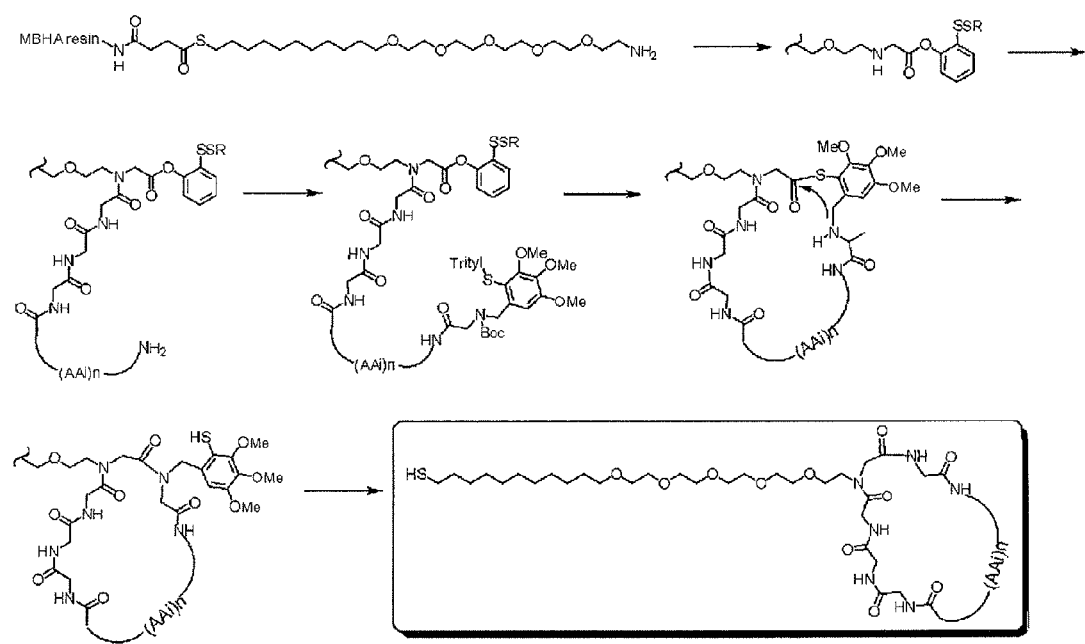
FIG. 13 is a schematic of a method for making and immobilizing cyclic peptide alkanethiols on gold films according to the present invention.

Referring to FIGS. 11 and 12, the present invention may also be used for chemoselective ligation for immobilizing linear peptides in aqueous buffer. As seen in FIG. 11, chemoselective chemistry may be used to immobilize peptides or proteins. The chemoselective reaction is between an optimized squarate ester and a cystesine amino acid. The present reaction offers three important properties and one unique aspect for working with proteins and whole mammalian cells. First, this reaction proceeds in entirely aqueous buffer. Second, this reaction proceeds with exclusive selectivity towards N-terminus cysteine of a peptide or a protein. Third, this reaction is not degraded by the key relevant enzyme in mammalian cells. All of these properties are particularly essential for immobilizing oriented peptides or proteins on surfaces, as seen in FIG. 8. Furthermore, this ligation tolerates the presence of internal cysteines in a peptide of interest, which is a capability that is lacking in conventional methods such as maleimide coupling chemistry. Peptide chips are also very useful for screening bio-active segments within a protein and play a key role in drug development. FIG. 13 depicts a general method for making and immobilizing cyclic peptide alkanethiols on gold films 16 according to the present invention that facilitates a wide range of applications in screening assays. FIG. 12A shows that mammalian cells 3T3 fibroblasts were immobilized on the bio-inert SAMs only when peptides containing Arginine-Glycine-Aspartic Acid (RGD) was used to react with the surface. In particular, the immobilizing peptides having N-terminus cysteine and other amino acids supported specific cell adhesions on self-assembled monolayers according to the present invention. Cell adhesion was observed when peptides containing tripeptide Arginine-glycine-aspartic acid (RGD) was used, but not when other peptides (control) were used.

Figure 14:
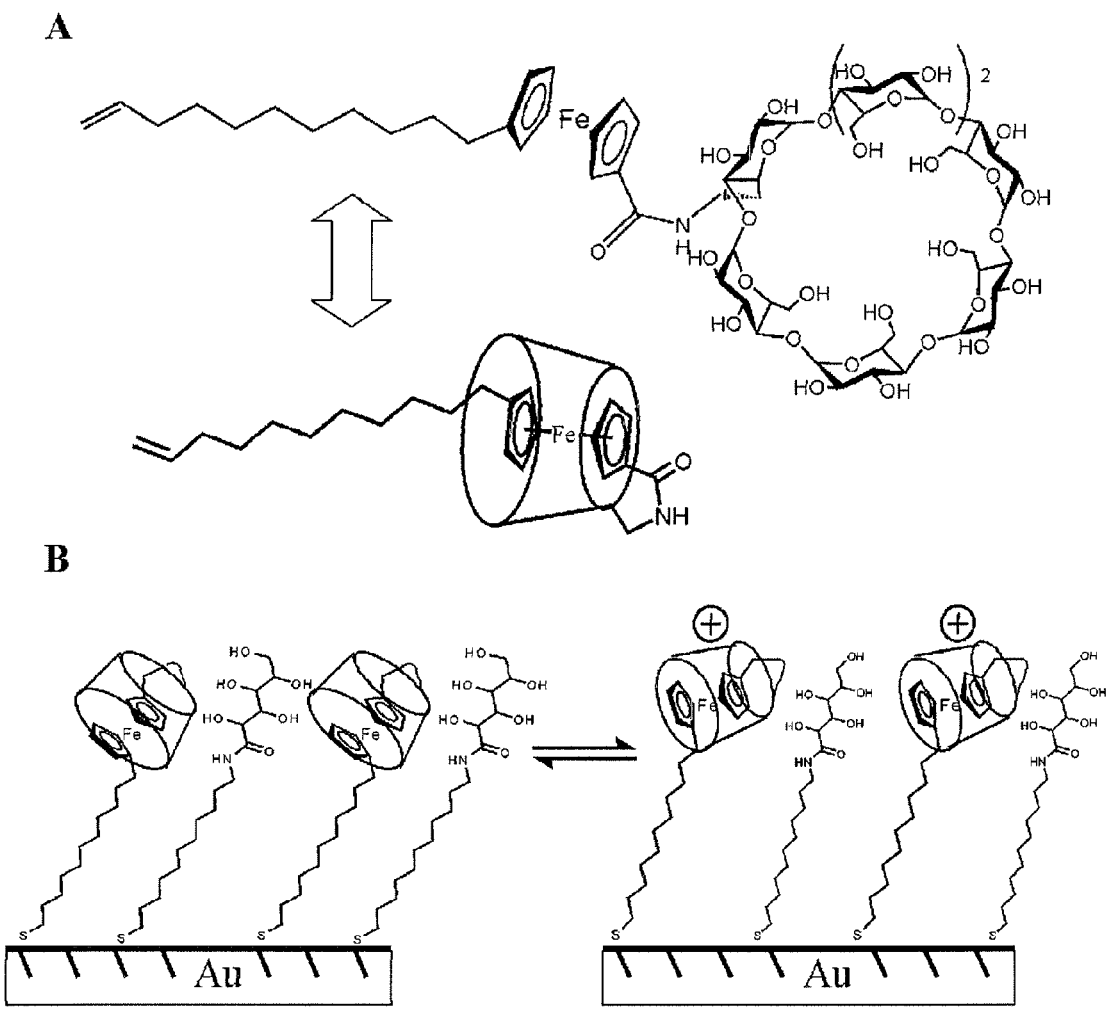
FIGS. 14A and B are schematics of amphiphiles and SAM based on the covalently caged ferrocene inside a β-CD according to the present invention.
FIG. 14C shows the electrochemical reactivity (cyclicvoltammogram) of SAM presenting covalently caged ferrocene inside a β-CD.
Figure 14C:
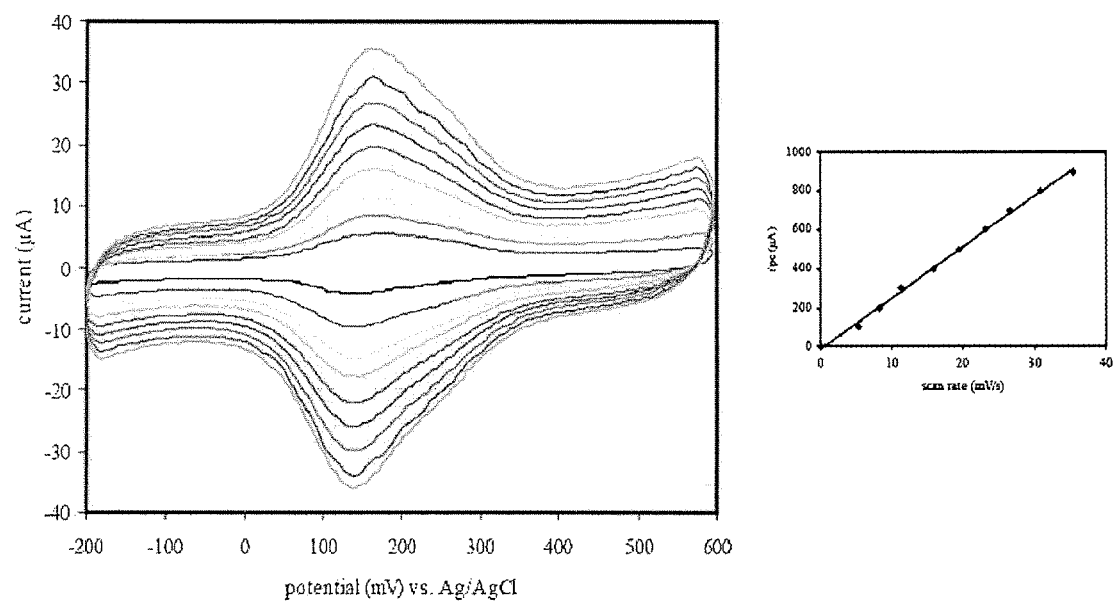

Referring to FIGS. 14A and B, the present invention also encompasses a bio-compatible redox based on caged ferrocene groups. Although the ferrocene molecule has been thought to be very useful since it was the subject of a Nobel Prize in the 1950s, only limited uses have been developed by making chiral derivatives of ferrocene and using them as asymmetric catalysts. One major limitation in the use of ferrocene is the fact that its oxidatized form, ferrocenium, is highly unstable in the presence of even weak nucleophiles, such as chloride ions, and thus the switching capability of the reversible redox of ferrocene is sabotaged. The present invention includes a chemical strategy to cage the ferrocene inside another organic molecule so that the ferrocenium ion can be protected from nucleophiles. For example, there is seen in FIG. 14A, an amphiphile based on a caged ferrocene according to the present invention that is protected from decomposition by nucleophilic attack of anions. There is seen in FIG. 14B, a SAM based on caged ferrocene that may be implemented with gold film 16 of slide 14 according to the present invention. The cyclic voltammograms of SAM presenting CD-caged ferrocene in 1.0 M HClO4 at the sweep rate from 100~900 mV/s of FIG. 14C show that the CD-Caged ferrocene is electroactive when immobilized on self-assembled monolayers. The insert shows the plots of anodic peal current of 1-modified gold SAM against the scan rate.

The present invention offers unprecedented control of structure and gradient density at the same time. Because of the well-ordered structure of SAMs on gold, the unique and useful chemical properties are retained. At the same time, because of the control of surface topography with a gradient at nanometer-scale, a chemical gradient is established. The present invention also offers compatibility with a wide range of chemistry. The integration of different terminal functional groups with gradient nanotopography turns useful functions into a chemical gradient on surfaces. The present invention further includes compatibility with a wide range of applications. Because of the sophistication of monolayer chemistry and the control of nanometer-scale topography, bio-assays including protein-protein binding, protein-small molecule

What is claimed is:

1. A method of forming a nanotopographic surface, comprising the steps of:
   providing a substrate aligned along a first plane;
   positioning a source for depositing a metal film on said substrate at a predetermined minimum angle of incidence to said plane of said substrate;
   tilting said substrate to align said substrate along a second plane intersecting said first plane at a predetermined offset angle;
   depositing a metal film on said substrate at said predetermined minimum angle of incidence to said substrate; and
   forming a self-assembling monolayer on said metal film, wherein said self-assembling monolayer includes a squarate ester.

2. The method of claim 1, wherein said metal film comprises gold.

3. The method of claim 2, wherein said predetermined minimum angle of incidence is thirty-seven degrees.

4. The method of claim 1, wherein said source is further positioned to deposit metal film on said substrate at a predetermined maximum angle of incidence.

5. The method of claim 4, wherein said predetermined maximum angle of incidence is fifty-nine degrees.

6. A method of forming a nanotopographic surface, comprising the steps of:
   providing a substrate;
   positioning a source for depositing a metal film on said substrate at a predetermined minimum angle of incidence to said substrate;
   depositing a metal film on said substrate at said predetermined minimum angle of incidence to said substrate; and
   forming a self-assembling monolayer on said metal film, wherein said self-assembling monolayer includes a squarate ester.

7. The method of claim 6, wherein said squarate ester is a cyclic squarate ester having the following formula:

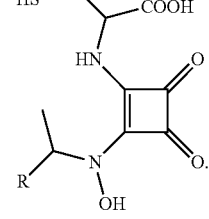

8. The method of claim 7, further comprising the step of ligating said squarate ester to a protein including an N-terminus cysteine.

9. The method of claim 8, wherein the step of ligating said squarate ester to a protein is performed in an aqueous buffer.

10. The method of claim 8, wherein the squarate ester is ligated only to said N-terminus cysteine.

* * * * *